United States Patent
Morita et al.

(10) Patent No.: US 9,855,013 B2
(45) Date of Patent: Jan. 2, 2018

(54) RADIOGRAPHY SYSTEM AND RADIOGRAPHY METHOD

(71) Applicant: FUJIFILM Corporation, Tokyo (JP)

(72) Inventors: Seiki Morita, Ashigarakami-gun (JP); Takaaki Higuchi, Ashigarakami-gun (JP); Masataka Sugahara, Ashigarakami-gun (JP); Wataru Sasaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 14/867,871

(22) Filed: Sep. 28, 2015

(65) Prior Publication Data

US 2016/0015333 A1 Jan. 21, 2016

Related U.S. Application Data

(63) Continuation of application No. PCT/JP2014/057230, filed on Mar. 18, 2014.

(30) Foreign Application Priority Data

Mar. 29, 2013 (JP) ................. 2013-073588

(51) Int. Cl.
*A61B 6/02* (2006.01)
*A61B 6/04* (2006.01)
*A61B 6/00* (2006.01)

(52) U.S. Cl.
CPC .............. *A61B 6/025* (2013.01); *A61B 6/502* (2013.01); *A61B 6/5205* (2013.01); *A61B 6/54* (2013.01);
(Continued)

(58) Field of Classification Search
None
See application file for complete search history.

(56) References Cited

U.S. PATENT DOCUMENTS 7,313,219 B2 * 12/2007 Endo .................... A61B 6/4476
378/22
2008/0108895 A1 5/2008 Sabol et al.
(Continued)

FOREIGN PATENT DOCUMENTS

| EP | 2 213 234 A1 | 8/2010 |
| JP | 2008-114064 A | 5/2008 |
| JP | 2010-172527 A | 8/2010 |

OTHER PUBLICATIONS

Extended European Search Report dated Mar. 10, 2016 in corresponding European Application No. 14775648.0.
(Continued)

*Primary Examiner* — Hoon Song
(74) *Attorney, Agent, or Firm* — Birch, Stewart, Kolasch & Birch, LLP

(57) ABSTRACT

A radiography system includes an imaging controller, a reconstruction processor, a process sequence controller and a display section. The imaging controller controls a radiation source to move in a range of a designated sweep angle and project X-rays at different angles to an imaging subject, while controlling a flat panel detector to acquire a set of projection images. The reconstruction processor uses the set of projection images to produce a plurality of tomographic images for use in diagnosis. The process sequence controller determines a parameter for sorting the plurality of tomographic images into first and second groups according to the sweep angle of the radiation source so as the first group of tomographic images to be produced prior to the second group of tomographic images. The display section displays at least the first group of tomographic images.

8 Claims, 8 Drawing Sheets

(52) U.S. Cl.
CPC ........... *A61B 6/0414* (2013.01); *A61B 6/4233* (2013.01); *A61B 6/463* (2013.01); *A61B 6/547* (2013.01)

(56) References Cited

U.S. PATENT DOCUMENTS

2010/0195789 A1* 8/2010 Kanagawa ........... G01N 23/046
378/11
2013/0148779 A1* 6/2013 Notohara ............... A61B 6/025
378/22

OTHER PUBLICATIONS

International Search Report, issued in PCT/JP2014/057230, dated Jun. 3, 2014.
Written Opinion of the International Searching Authority for PCT/JP2014/057230, dated Jun. 3, 2014.

* cited by examiner

|  | θ (deg) | M | N | ... | NUMBER FOR THINNING |
|---|---|---|---|---|---|
| STANDARD MODE | 20 | 60 | 129 | ... | 0 |
| HIGH-SPEED MODE | 7.5 | 60 | 129 | ... | 1 |

RADIOGRAPHY SYSTEM AND RADIOGRAPHY METHOD

CROSS-REFERENCE TO RELATED APPLICATIONS

This application is a Continuation of PCT International Application No. PCT/JP2014/057230 filed on Mar. 18, 2014, which claims priority under 35 U.S.C §119(a) to Japanese Patent Application No. 2013-073588 filed Mar. 29, 2013. The above application is hereby expressly incorporated by reference, in its entirety, into the present application.

BACKGROUND OF THE INVENTION

1. Field of the Invention

The present invention relates to a radiography system and a radiography method, wherein tomographic images of a subject are obtained through reconstruction of radiographic images which are acquired from the subject by projecting radiation at different projection angles.

2. Description Related to the Prior Art

Radiography systems have been widely spread, which are each equipped with a radiation source for projecting radiation (e.g. x-rays) to a subject and a radiographic image detector for detecting radiographic images of the subject by detecting radiation that has penetrated the subject and falls on individual pixels of the detectors, which are arranged in a two-dimensional array. The radiographic image detected by the radiographic image detector is a so-called projection image, wherein information on the subject across the depth of the subject, i.e. in the radiation penetrating direction is superposed. Therefore, from a projection image of a subject (e.g. a patient for diagnosis), it is difficult to perceive multiple diseased tissues or the like, which may exist at different depths in the subject, distinguishably from each other.

Meanwhile, radiography systems have been known, wherein the radiation source and the radiographic image detector are configured to be movable in position or variable in projection angle so as to image a subject at different projection angles and thus acquire a sequence of projection images, and the sequence of projection images are subjected to a reconstruction process to produce tomographic images of the subject sliced at desired depths (US 2008/0108895 A1 corresponding to JPA No. 2008-114064 and US 2010/0195789 A1 corresponding to JPA No. 2010-172527). The imaging method in these radiography systems is called tomosynthesis. In comparison with the projection image, the tomographic image acquired by the tomosynthesis is improved in resolution in the direction across the depth of the subject, and it is possible to observe a diseased tissue or the like that exists at a certain depth distinguishably from another diseased tissue or the like that exists at a different depth.

Radiographic image acquisition is usually carried out by a radiologist according to a request from a doctor. After the radiographic image acquisition, the radiologist will examine the acquired projection images or tomographic images before submitting the images to the doctor (or to an image server or the like that the doctor can access for reference), in order to determine whether the acquired images are good or not, that is, whether the quality of the acquired images is adequate for use in diagnosis (hereinafter this examination will be referred to as the image examination).

Likewise, the image examination is carried out in the tomosynthesis. As for a tomosynthesis image acquisition, a plurality of tomographic images produced with regard to different positions in a subject, for example sequentially from one side to the other side of the subject, are to be inspected such that the inspected images are not biased in relation to the positions in the subject, thereby to determine on the basis of blurs, noise level, etc. of the tomographic images whether the image acquisition is successful or failed. For accurate determination on the success or failure of the image acquisition, it is usual to carry out the image examination of all tomographic images after the production thereof.

However, for the tomosynthesis, it is necessary to produce several tens to more than one hundred tomographic images, and it takes a long time to complete production of such a great number of tomographic images. The time waiting for the production of tomographic images is one of causes that waste time taken for the image examination.

The tomosynthesis imaging system according to US 2008/0108895 A1 automatically determines the sweep angle of the radiation source and the radiation dose, etc. by designated desirable image characteristics (such as resolution and noise level). This method may be effective to save the preparation time required for acquiring a set of projection images which are used for production of tomographic images, but could not reduce the time taken for the image examination.

The tomosynthesis imaging system according to US 2010/0195789 A1 produces an incomplete tomographic image using part of a set of projection images, to enable the image examination based on the incomplete tomographic image. However, as being produced using a reduced number of projection images, the incomplete tomographic image is inferior in quality to a tomographic image that is produced using all of the series of projection images. Therefore, depending on the skills in imaging and examining the tomographic images, there may be cases where the radiologist cannot exactly determine whether the image acquisition is successful or not on the basis of the incomplete tomographic image. Even while an incomplete tomographic image is displayed faster than a complete tomographic image and thus the radiologist may feel released from the stress of waiting for the production of an individual tomographic image for examination, the radiologist ends up waiting for the completion of all tomographic images of a subject because it is necessary to examine a plurality of tomographic images that relate to unbiased positions of the subject. Accordingly, the feature of producing and displaying incomplete tomographic images could not reduce the total time required for the image examination.

SUMMARY OF THE INVENTION

An object of the present invention is to provide a radiography system and a radiography method, which enable an exact image examination while reducing the time required therefor.

A radiography system in accordance with the present invention comprises a radiation source, a radiographic image detector, an imaging controller, a reconstruction processor, a process sequence controller and a display device. The radiation source is mounted movable to multiple positions of different projection angles relative to an imaging subject which is placed at a predetermined position. The radiographic image detector detect a radiographic image of the subject by detecting radioactive rays that have penetrated the subject. The imaging controller controls the radiation source to move within a range of a designated sweep angle and project radioactive rays toward the subject at different projection angles while controlling the radiographic image detector to detect a set of radiographic images each at a different projection angle. The reconstruction processor reconstructs the set of radiographic images acquired from the subject at multiple projection angles so as to produce a plurality of tomographic images of the subject, which are used for diagnosis. The process sequence controller determines a parameter for sorting the plurality of tomographic images into a first group and a second group according to the sweep angle and controls the reconstruction processor on the basis of the parameter so as to produce the first group of tomographic images prior to the second group of tomographic images. The display device displays at least the first group of tomographic images for determination on whether the tomographic images are adequate for use in diagnosis.

Preferably, the process sequence controller determines the parameter such that the first group of tomographic images are selected from the plurality of tomographic images at intervals of a predetermined number.

Preferably, the process sequence controller determines the parameter such that the number of tomographic images included in the first group decreases with the smaller sweep angle.

The radiography system in accordance with the present invention is preferably provided with at least two imaging modes, including a first imaging mode wherein the sweep angle is set at a predetermined value, and a second imaging mode wherein the sweep angle is set at a smaller value than in the first imaging mode. Then, the process sequence controller preferably determines the parameter such that the number of tomographic images included in the first group is reduced in the second imaging mode in comparison with the first imaging mode. Furthermore, the process sequence controller preferably determines the parameter such that all of the plurality of tomographic images are sorted into the first tomographic image group when the first imaging mode is selected.

When it is determined on the basis of the first group of tomographic images displayed on the display device that the tomographic images are adequate for use in diagnosis, the display device preferably displays a screen for making another image acquisition and the reconstruction processor preferably produces the second group of tomographic images in the background.

When it is determined on the basis of the first group of tomographic images displayed on the display device that the tomographic images are inadequate for use in diagnosis, the reconstruction processor preferably quits producing the second group of tomographic images.

A radiography method in accordance with the present invention comprises an imaging step, a parameter calculation step, a tomographic image production step and a tomographic image display step. In the imaging step, a radiation source, which is mounted movable to multiple positions of different projection angles relative to an imaging subject, which is placed at a predetermined position, is moved within a range of a designated sweep angle while projecting radioactive rays toward the subject at different projection angles, whereas the radiographic image detector detects a set of radiographic images each at a different projection angle. In the parameter calculation step, a parameter is determined according to the sweep angle. The parameter is for sorting a plurality of tomographic images to be produced in the tomographic image production step into a first group and a second group. The tomographic image production step is a step wherein a plurality of tomographic images of the subject, which are used for diagnosis, are produced by reconstructing the set of radiographic images acquired from the subject at multiple projection angles, and wherein the plurality of tomographic images to be produced are sorted into the first group and the second group according to the parameter, and the first group of tomographic images are produced prior to the second group of tomographic images. In the tomographic image display step, at least the first group of tomographic images are displayed for determination on whether the tomographic images are adequate for use in diagnosis or not.

In the radiography system and the radiography method in accordance with the present invention, minimum tomographic images required for the image examination are selected to be produced and displayed preferentially according to the sweep angle from among the tomographic images to be produced for diagnosis, enabling completing the image examination in a shorter time while ensuring the precision thereof.

BRIEF DESCRIPTION OF THE DRAWINGS

The above and other objects and advantages of the present invention will be more apparent from the following detailed description of the preferred embodiments when read in connection with the accompanying drawings, wherein.

DESCRIPTION OF THE PREFERRED EMBODIMENTS

Figure 1:
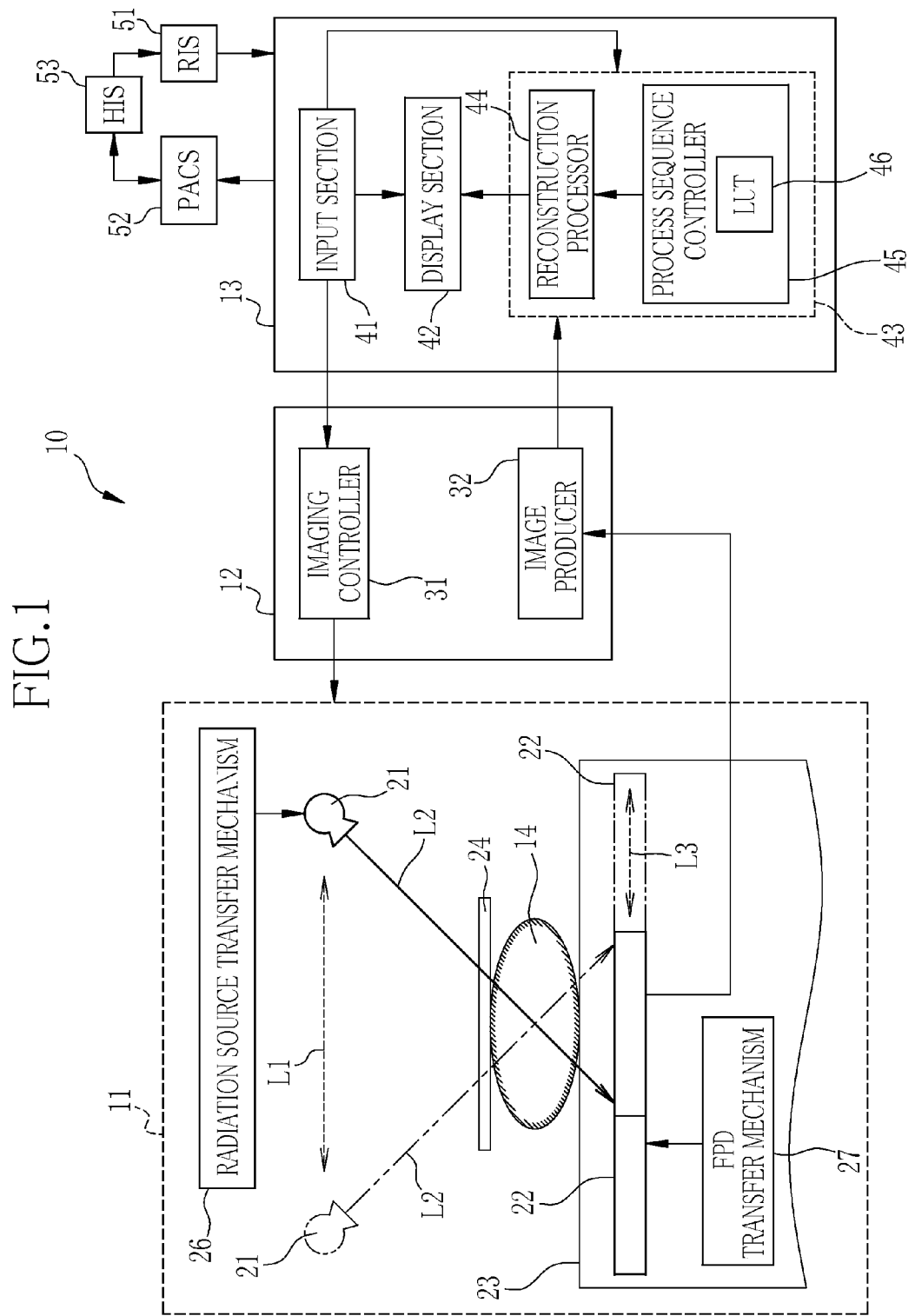
FIG. 1 is a block diagram illustrating a structure of a radiography system.

As shown in FIG. 1, a radiography system 10 is typically equipped with an imaging unit 11, a control unit 12 for controlling the imaging unit 11, and a console 13 for operating input/output of various data and the like between the control unit 12 and other external devices.

In this example, the imaging unit 11 is a digital mammography apparatus which is mainly provided with a radiation source 21, a flat panel detector (FPD) 22 as a radiographic image detector, an imaging stage 23 and a pressing plate 24, wherein a breast mass is an imaging subject 14. The subject 14 is set on the imaging stage 23 and pressed onto the imaging stage 23 by the pressing plate 24 which is movable relative to the imaging stage 23, so as to be imaged in a flatten-out condition.

The radiation source 21 generates X-rays. The quantity and quality of X-rays generated from the radiation source 21 are adjustable by means of tube voltage and tube current. The radiation source 21 is mounted to a radiation source transfer mechanism 26 such that the radiation source 21 is movable in parallel to an obverse surface of the imaging stage 23, as indicated by an arrow L1. While moving the radiation source 21 in parallel to the imaging stage 23, the radiation source transfer mechanism 26 also turns the radiation source 21 in cooperation with the parallel movement thereof such that the X-ray projecting direction L2 of the radiation source 21 is always oriented toward the subject 14.

The FPD 22 is an indirect-conversion type radiographic image detector which has a scintillator for converting X-rays into visible light and a TFT panel that photoelectrically converts the light emitted from the scintillator into an image signal in each pixel. The FPD 22 is mounted to an FPD transfer mechanism 27 which is provided in the imaging stage 23, so that the FPD 22 is movable in parallel to the obverse surface of the imaging stage 23, as indicated by an arrow L3. The FPD 22 is moved correspondingly to the position and the projecting direction of the radiation source 21 such that the FPD 22 is always located in a position where the FPD 22 detects an X-ray image of the subject 14 from X-rays that have penetrated the subject 14. The radiation source 21 and the FPD 22 are mounted movable in the manner as set above, enabling the radiography system 10 to make not only a projection image acquisition but also a tomosynthesis image acquisition.

The control unit 12 is provided with an imaging controller 31 and an image producer 32. The imaging controller 31 controls components of the imaging unit 11 by inputting various signals for controlling the respective operations of the components of the imaging unit 11 on the basis of imaging parameters and the like, which are input through an input section 41 of the console 13. For example, the imaging controller 31 controls the tube voltage and the tube current of the radiation source 21 to control the quantity and the quality of X-rays generated from the radiation source 21.

The imaging controller 31 controls the position and the projecting direction of the radiation source 21 and the position of the FPD 22 synchronously with each other through the radiation source transfer mechanism 26 and the FPD transfer mechanism 27. The imaging controller 31 also controls operation of the pressing plate 24, timing of X-ray generation from the radiation source 21, timing of imaging on the FPD 22 and synchronization of these operations. The imaging controller 31 thus controls the components of the imaging unit 11 to make, for example, a tomosynthesis image acquisition, acquiring a set of projection images of the subject 14 to produce tomographic images of the subject 14 therefrom.

The imaging controller 31 not only controls producing tomographic images but is also capable of controlling the imaging unit 11 to acquire an ordinary projection image that is directly used for diagnosis. Note that operation devices (not shown), including a switch for instructing the start of an image acquisition, are connected to the imaging controller 31.

The image producer 32 produces a projection image based on the image signals output from the FPD 22. The projection image produced by the image producer 32 is input to an image processor 43 of the console 13. The projection image produced by the image producer 32 is compliant with the DICOM (Digital Imaging and Communication in Medicine) standard; the image producer 32 records various meta-information in the header of each projection image. For example, the meta-information recorded in the header of each projection image includes date of imaging, name, age, gender of patient (subject), imaged site and serial number.

When making a tomosynthesis image acquisition by the radiography system 10, a plurality of projection images obtained for producing tomographic images are identified as a set of projection images on the basis of meta-information recorded in the header of each image. Likewise, on the basis of the meta-information, the individual projection images of the set are identified with respect to respective projection angles (positions of the subject 14 and the FPD 22 relative to the subject 14), etc.

The console 13 is provide with the input section 41, a display unit 42 and the image processor 43. The console 13 is linked to a Radiology Information System (RIS) 51, a Picture Archiving and Communication System (PACS) 52 and a Hospital Information System (HIS) 53.

The input section 41 is constituted of various input devices, such as a keyboard, operation buttons and pointing devices like a mouse. The radiologist uses the input section 41 to input various information to be recorded as meta-information about the projection images and imaging parameters for controlling the operation of the radiography system 10 into the radiography system 10 on the basis of an order for imaging which is received from a doctor. In a typical example, the order for imaging includes name and age of the subject 14, the imaging site, the kind of imaging (a designated method of imaging, i.e. imaging for the tomosynthesis or imaging for obtaining an ordinary projection image, etc.), whereas the imaging parameters include tube voltage and tube current of the radiation source 21 and a selected operation mode corresponding to the kind of imaging.

When making a tomosynthesis image acquisition, a sweep angle of the radiation source 21 (the maximum angle of movement of the radiation source 21) and the number of tomographic images to be produced are also input as the imaging parameters. When processing a projection image or other images for rendering, selection of various processes and parameter settings are carried out through the input section 41.

When the input section 41 receives an order for imaging from the RIS 51, the input section 41 automatically inputs part of various information to be recorded as meta-information on the projection images and imaging parameters. Several sets of frequently-used imaging parameters are previously stored (preset) as imaging modes in the radiography system 10. When one of the preset imaging modes is selected through the input section 41, the imaging parameters corresponding to the selected imaging mode are automatically input in the imaging controller 31 and the image processor 43.

In an example, the display section 42 is composed of a liquid crystal display (LCD) monitor and a display controller (not shown 9 for controlling displaying on the LCD monitor, etc., and displays input screens for inputting an order for imaging and imaging parameters, acquired projection images and tomographic images produced through a tomosynthesis image acquisition, etc. The display section 42 consists of a single monitor or multiple monitors. The image examination for determining whether an image acquisition is successful or not is done by the radiologist examining acquired images on the display section 42. The image examination includes inspecting a plurality of tomographic images, which are produced in a range from an obverse side (the side facing the radiation source 21) to a reverse side (the side facing the FPD 22) of the subject 14, through the whole range, and determining whether the image acquisition is successful or failed on the basis of blurs, noise level, etc. of the inspected images. The blur is caused, for example, by a movement (body movement) of the patient during the imaging. When the radiologist determines as a result of the image examination that the image acquisition is successful, the radiologist transmits the tomographic images to the PACS 52, completing the tomosynthesis image acquisition. If determines that the image acquisition is failed, for example, because of blurry images, the radiologist restarts image acquisition of a set of projection images of the subject 14 from the beginning.

The image processor 43 processes the projection images from the image producer 32 for various image-rendering. For example, according to commands entered through the input section 41, the image processor 43 selectively performs noise-reduction by averaging or the like, edge-enhancing by bypass-filtering or the like, smoothing, contrast-adjusting by graduation-conversion or the like. Depending on the setup display mode of the display section 42, the image processor 43 may produce size-reduced images (thumbnails) of the projection images from the image producer 32, for displaying the size-reduced images in a list.

The image processor 43 further includes a reconstruction processor 44 and a process sequence controller 45, which are used for the tomosynthesis imaging.

The reconstruction controller 44 reconstructs a set of projection images obtained by a tomosynthesis image acquisition so as to produce tomographic images (which may be called reconstructed images) of the subject 14. The reconstruction process for producing tomographic images in the tomosynthesis is carried out according to a shift-and-add (SA) method, a filtered back projection (FBP) method, or the like. The production method for the tomographic images, the number of images to be produced (the slice pitch of the tomographic images) and other conditions are determined according to values entered as imaging parameters through the input section 41. The tomographic images produced by the reconstruction controller 44 are used for diagnosis as well as for the image examination. Diagnosis here means pathological determination by a doctor through radiographic image interpretation, for example, as to whether there is a tumor in the subject or not. On the contrary, the image examination performed by the radiologist is merely for evaluation on the adequacy of the acquired images in quality, such as the level of blurs or noises, and any pathological determination is made on the image examination.

The reconstruction controller 44 produces a plurality of tomographic images at a tomosynthesis image acquisition. The reconstruction controller 44 is capable of producing a group of tomographic images first among all tomographic images to be produced at one tomosynthesis image acquisition, and thereafter remaining tomographic images, wherein the tomographic images to be produced first are selected depending on the number for thinning that is determined by the process sequence controller 45. Hereinafter, a group of tomographic images produced first will be referred to as the first group of tomographic images, whereas a group of tomographic images produced afterward will be referred to as the second group of tomographic images.

Tomographic images of the first and second groups are displayed sequentially on the display section 42 basically soon after each image production by the reconstruction controller 44. However, although at least all of tomographic images of the first group will be displayed on the display section 42, there may be cases where some or all of tomographic images of the second group will not be displayed on the display section 42.

For instance, there is a case where the radiologist determines to terminate the image examination merely from the observation on tomographic images of the first group displayed on the display section 42. If the radiologist determines the image acquisition to be successful as a result of the image examination on the tomographic images of the first group and inputs an instruction to transmit the tomographic images to the PACS 52 before the tomographic images of the second group are produced, the tomographic images of the second group are not displayed on the display section 42, but the display section 42 displays a screen for an image acquisition from the next subject. At that time, the radiography system 10 apparently performs other operations such as a preparatory process for imaging, while producing the tomographic images of the second group as a background process without displaying these images on the display section 42.

The process sequence controller 45 obtains imaging parameters for a tomosynthesis image acquisition that are input from the input section 41, determines the number for thinning on the basis of the obtained imaging parameters, and controls the production sequence for tomographic images to be produced by the reconstruction controller 44. Specifically, based on the sweep angle of the radiation source 21, the process sequence controller 45 determines the number for thinning that represents the interval for sorting tomographic images into the first group. According to the number for thinning, the reconstruction controller 44 thins out those tomographic images to be sorted into the second group from among all tomographic images to be produced at one tomosynthesis image acquisition, and sorts the remaining tomographic images into the first group. That is, the number for thinning is a parameter for sorting out all the tomographic images into the first and second groups.

For example, provided that a number N slices of tomographic images are totally produced at one tomosynthesis image acquisition and the number for thinning is determined to be "1", the production of even-numbered tomographic images (the second, fourth, sixth, . . . tomographic images in the order of the slice positions thereof from the side facing the radiation source 21) are skipped as the second group, while odd-numbered (the first, third, fifth, . . . ) tomographic images are produced as the first group prior to the second group. If the number for thinning is "2", every third (e.g. the first, fourth, seventh, . . . ) tomographic images are sorted into the first group and produced first, and the remaining (the second, third, fifth, sixth, . . . ) tomographic images are sorted into the second group to be produced afterward. The same applies to cases where the number for thinning is "3" or more. Note that the number for thinning can be "0", wherein any tomographic images are not sorted into the second group, but all of N tomographic images are sorted into the first group.

The process sequence controller 45 is previously provided with a lookup table (LUT) 46 that correlates sweep angles of the radiation source 21 with numbers for thinning, so that the process sequence controller 45 determines the number for thinning with reference to the LUT 46, depending on the sweep angle of the radiation source 21 which is set as an imaging parameter. For example, the LUT 46 correlates a predetermined selectable sweep angle with a number for thinning each individually. The sweep angles and numbers for thinning are set up to have such a relation that the higher number for thinning is assigned to the smaller sweep angle in the LUT 46. The reason will be set forth later.

The number for thinning may be determined as one of the imaging parameters stored as the preset imaging modes. In that case, the process sequence controller 45 inputs the number for thinning obtained as one imaging parameter from the input section 41 to the reconstruction controller 44 when one of the preset imaging modes is selected through the input section 41. Since the number for thinning in each preset imaging mode is determined to coincide with one of the numbers for thinning which are memorized in the LUT 46, the process of obtaining the number for thinning according to the selected imaging mode is equivalent to the process of obtaining the sweep angle as one imaging parameter and determining the number for thinning with reference to the LUT 46.

The RIS 51 is a system for managing image acquisitions by radiological apparatuses such as the radiography system 10, radiological examinations, reservations for treatments, and the results of image acquisitions and examinations. The RIS 51 receives information about patients and orders for imaging from doctors over the HIS 53, and inputs the orders for imaging and the information about patients, etc. in one radiological apparatus (the radiography system 10) designated, for example, on the RIS 51 by a radiologist.

The PACS 52 is for storing medical images including radiographic images and consolidates the management thereof. In response to a request from the HIS 53 or the RIS 51, the PACS 52 transmits tomographic images and other images acquired by the radiography system 10 in order to display these images. The radiography system 10 transmits the acquired projection images and tomographic images to the PACS 52.

The HIS 53 is an integrative managing system that includes the management of electronic medical records. For example, orders for imaging are input on the HIS 53.

Figure 2:
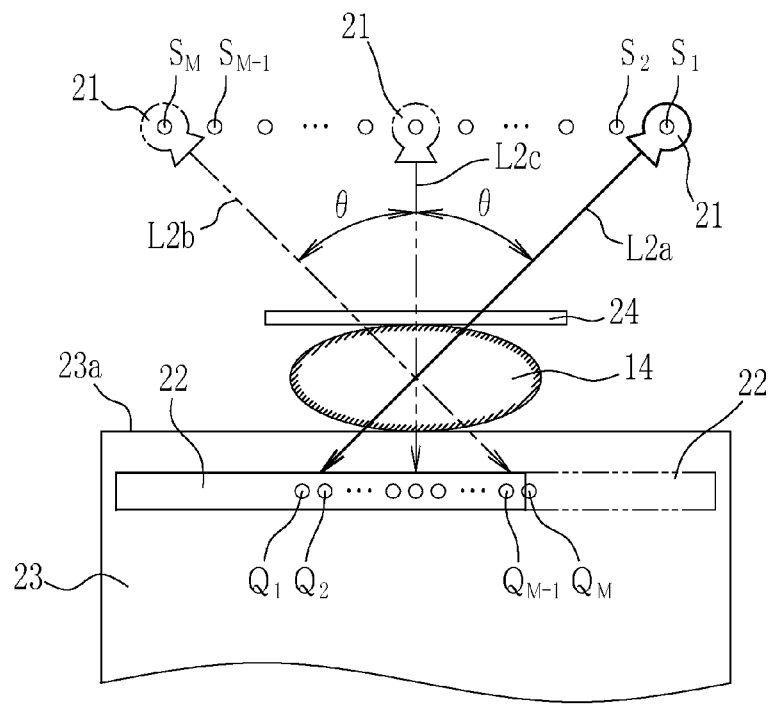
FIG. 2 is an explanatory diagram illustrating the operation of a radiation source and a FPD (flat panel detector)

As shown in FIG. 2, for a tomosynthesis image acquisition, the position Sk of a center (the origin of radiation) of the radiation source 21 is moved intermittently at determined pitches from a start position $S_1$ (k=1) to an end position $S_M$ (k=M). In addition, the radiation source 21 is turned to change the projecting direction from each position Sk toward the subject 14 such that optical axes of X-rays projected from the respective positions Sk intersect at a single point inside the subject 14. "M" represents an integer that corresponds to the number of projection images obtained at the tomosynthesis image acquisition. In an example, the intervals between the adjacent positions Sk (the movement pitch of the radiation source 21) are constant, and the imaging controller 31 automatically determines the number M of projection images and the intervals between the positions Sk according to the sweep angle θ of the radiation source 21 and the number N of tomographic images to be produced, etc., which are designated as the imaging parameters.

The sweep angle θ of the radiation source 21 is one half the angle between a projecting direction L2a of X-rays from the radiation source 21 at the start position $S_1$ and a projecting direction L2b of X-rays from the radiation source 21 at the end position $S_M$. In other words, the sweep angle θ represents the respective angles θ of the projecting directions L2a and L2b relative to a projecting direction L2c that is perpendicular to the FPD 22 and the obverse surface 23a of the imaging stage 23.

The FPD 22 is also moved intermittently in correspondence with but in the opposite direction to the intermittent movement of the radiation source 21 such that a center of the FPD 22 is placed at positions Qk (k=1 to M) right across the subject 14 from the center of the radiation source 21 at the respective positions Sk. Thus, the X-rays projected from the radiation source 21 at the respective positions Sk penetrate the subject 14 and fall on the FPD 22, and thus the FPD 22 acquires a projection image of the subject 14 at a different projection angle. Consequently, a total number M of projection images are acquired at different projection angles as a set of projection images which are used for producing tomographic images.

Figure 3:
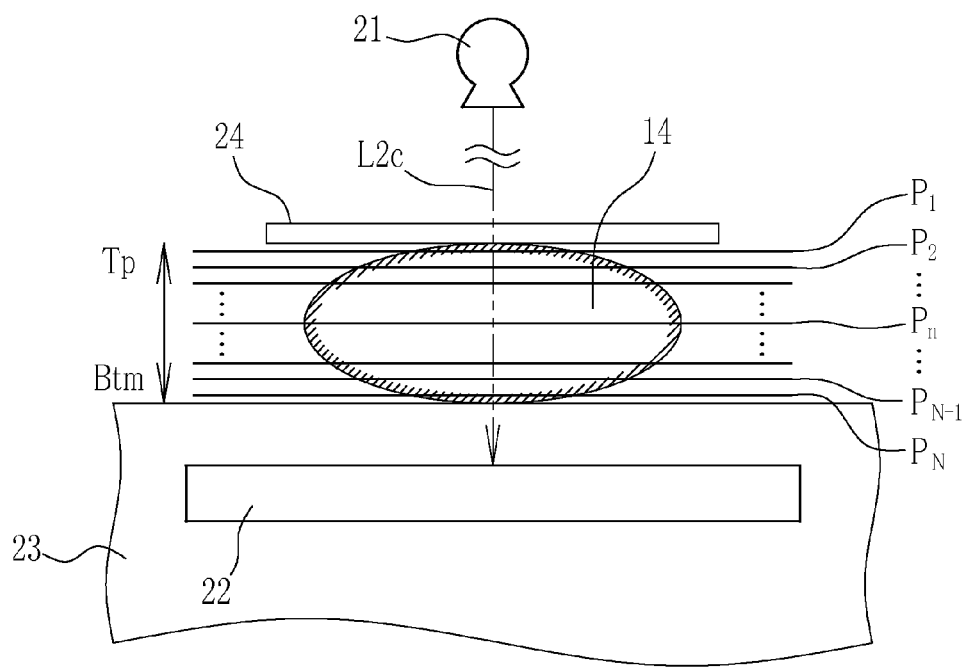
FIG. 3 is an explanatory diagram illustrating a relationship between an imaging subject and tomographic images.

As shown in FIG. 3, the reconstruction processor 44 produces a number N of tomographic images $P_n$ (n=1 to N) using a set of M projection images. The tomographic images $P_n$ correspond to slices through the subject 14 in the direction perpendicular to the projecting direction L2c, i.e., parallel to the plane of the FPD 22; the tomographic images are also called slice images. An integer "n" represents a slice position of each tomographic images through the subject 14, and increments from 1 to N in the order from the side facing the radiation source 21 (top side Tp) to the side facing the FPD 22 (bottom side Btm). Note that the interval between the slice positions (slice pitch) is constant. The slice pitch may, for example, be predetermined as an imaging parameter.

Figure 4:
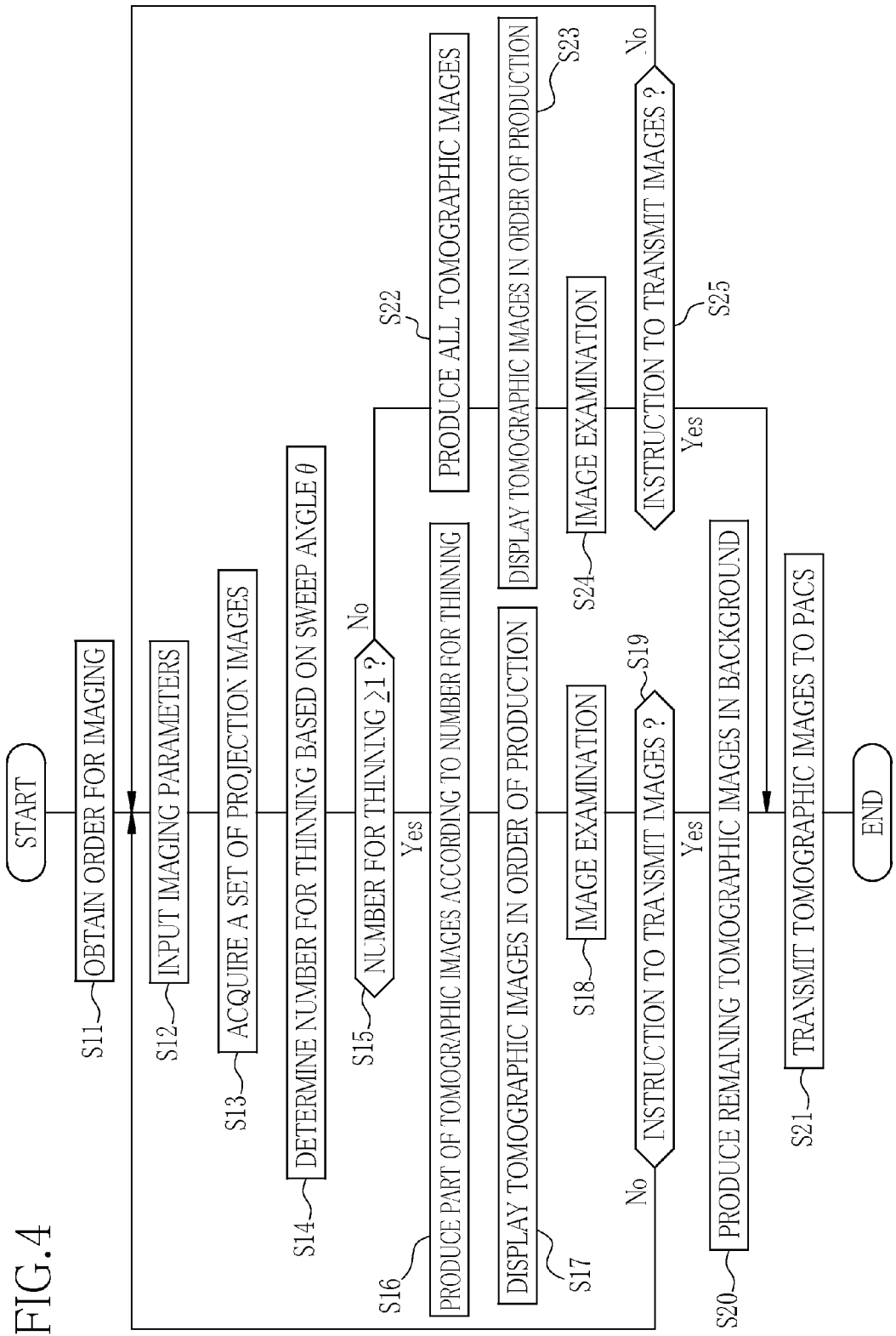
FIG. 4 is a flowchart illustrating an operation for a tomosynthesis image acquisition.

As shown in FIG. 4, when the radiography system 10 makes a tomosynthesis image acquisition, first the RIS 51 obtains an order for imaging from the HIS 53 (S11). On the basis of the obtained order for imaging, imaging parameters such as a sweep angle θ are input on the console 13 (S12). As shown for example in FIG. 5, the radiography system 10 has two kinds of preset imaging mode for the tomosynthesis image acquisition: a standard mode (first imaging mode) and a high-speed mode (second imaging mode). Therefore, part of the imaging parameters may be input automatically by selecting one of the imaging modes.

When the input of imaging parameters is complete, the subject 14 placed on the imaging stage 23 is fixed by being pressed by the pressing plate 24 onto the imaging stage 23. Thereafter upon an input of an instruction to start imaging, the imaging controller 31 controls the imaging unit 11 to move the radiation source 21 and the FPD 22 intermittently and acquire images from the subject 14 at respective positions in accordance with the setup imaging parameters (S13: imaging step). Thus, a set of projection images $P_n$ used for producing tomographic images are acquired and fed to the reconstruction processor 44.

When the set of projection images $P_n$ is obtained, the process sequence controller 45 obtains the sweep angle θ that has been input as one imaging parameter, and refers to the LUT 46 to determine the number for thinning (S14: parameter calculation step). If, however, one of the present imaging modes is selected at the step of inputting imaging parameters, the process sequence controller 45 does not obtain the sweep angle θ but directly obtains the number for thinning that is predetermined as an imaging parameter for the selected imaging mode. The process sequence controller 45 inputs the determined number for thinning in the reconstruction processor 44.

When the number for thinning is "1" or more (S15; Yes), the reconstruction processor 44 first produces parts of tomographic images (the first group of tomographic images) according to the number for thinning among all tomographic images $P_1$ to $P_N$ to be produced (S16: tomographic image production step). For example, if the high-speed mode is selected, the number for thinning is "1", so the reconstruction processor 44 first produces every second tomographic image $P_n$ among all tomographic images $P_1$ to $P_N$. For example, odd-numbered tomographic images $P_n$, wherein n 1, 3, 5, . . . , are produced as the first group of tomographic images sequentially in ascending order of n.

The first group of tomographic images $P_1$, $P_3$, $P_5$, . . . , as produced prior to other tomographic images, are sequentially displayed on the display unit 42 (S17: tomographic image display step). When all of the first group of tomographic images $P_1$, $P_3$, $P_5$, . . . have been completely produced and displayed on the display unit 42, the radiologist carries out the image examination of these images to determine the adequacy of the tomosynthesis image acquisition (S18). When the radiologist determines by the image examination that the image acquisition is successful, the radiologist pushes a transmission button 83 (refer to FIG. 8, etc.) to input an instruction to transmit the tomographic images $P_n$ to the PACS (S19; Yes). If the radiologist determines by the image examination that the image acquisition is failed, the radiologist pushes a re-imaging button 84 (refer to FIG. 8, etc.) to input an instruction to restart the image acquisition sequence from the beginning (S19; No).

When the instruction to transmit the images, the console 13 controls the display unit 42 to display a preparatory screen for the next tomosynthesis image acquisition, but in the background the reconstruction processor 44 produces the remaining tomographic images $P_n$ (=$P_2$, $P_4$, $P_6$, . . . ) which are sorted out to be produced later (the second group of tomographic images) sequentially in ascending order of n (S20). Thereafter when the second group of tomographic images have completely been produced, the console 13 transmits all tomographic images $P_1$ to $P_N$ to the PACS 52 (S21). Thus, one tomosynthesis image acquisition is complete.

Meanwhile, when the re-imaging instruction is input in the console 13, the display unit 42 is controlled to display a preparatory screen for remaking a tomosynthesis image acquisition. At that time, the reconstruction processor 44 cancels the production of the second group of tomographic images $P_2$, $P_4$, $P_6$, . . . . Then the radiologist, for example, changes the imaging parameters on the preparatory screen displayed on the display unit 42, and retries the tomosynthesis image acquisition.

If the number for thinning is "0" (S15; No), for example, when the standard mode (refer to FIG. 5) is selected at the time for inputting imaging parameters, the reconstruction processor 44 does not execute the thinning and produces all tomographic images $P_1$ to $P_N$ as the first group sequentially in ascending order of n (S22), and the produced tomographic images $P_n$ are sequentially displayed on the display unit 42 (S23).

When all of the tomographic images $P_1$ to $P_N$ have been produced and displayed on the display unit 42, the radiologist makes the image examination on these tomographic images $P_1$ to $P_N$ (S24) to determine the adequacy of tomosynthesis image acquisition. When the radiologist determines by the image examination that the image acquisition is successful, the radiologist pushes the transmission button 83 to input an instruction to transmit the tomographic images $P_n$ to the PACS 52 (S25; Yes). Then the console 13 causes the display unit 42 to display the preparatory screen for the next tomosynthesis image acquisition and transmits the produced tomographic images $P_1$ to $P_N$ to the PACS 52.

If the radiologist determines by the image examination that the image acquisition is failed, the radiologist pushes the re-imaging button 84 to input an instruction to restart the image acquisition sequence from the beginning (S25; No). In that case, the console 13 causes the display unit 42 to display the preparatory screen for re-imaging. Then the radiologist retries a tomosynthesis image acquisition, for example, after changing imaging parameters on the preparatory screen displayed on the display unit 42.

As described above, the radiography system 10 produces and displays the tomographic images which have sufficient quality for use in diagnosis as well, unlike conventional low quality images for the image examination which are produced using a reduced number of projection images or a simple algorithm, enabling the image examination with high accuracy (reliability).

In addition, the radiography system 10 sorts out all tomographic images $P_1$ to $P_N$ to be produced into the first group and the second group according to the number for thinning, and produces and displays the first group of tomographic images first for the shake of the image examination, whereas the second group of tomographic images are produced in the background. Therefore, in comparison with the case of displaying all tomographic images $P_1$ to $P_N$ for the image examination, it will take shorter time for the image examination.

For example, when the high-speed mode is selected, wherein the sweep angle θ is 7.5 degrees and 129 tomographic images $P_1$ to $P_{129}$ are to be produced (refer to FIG. 5), the number for thinning is "1". In this case, the reconstruction processor 44 produces every second tomographic images $P_n$ in ascending order of n. For example, odd-numbered tomographic images $P_1$, $P_3$, . . . , $P_{127}$, $P_{129}$ are sorted to be the first group, and even-numbered tomographic images $P_2$, $P_4$, . . . , $P_{126}$, $P_{128}$ are sorted to be the second group.

Figures 5, 6:
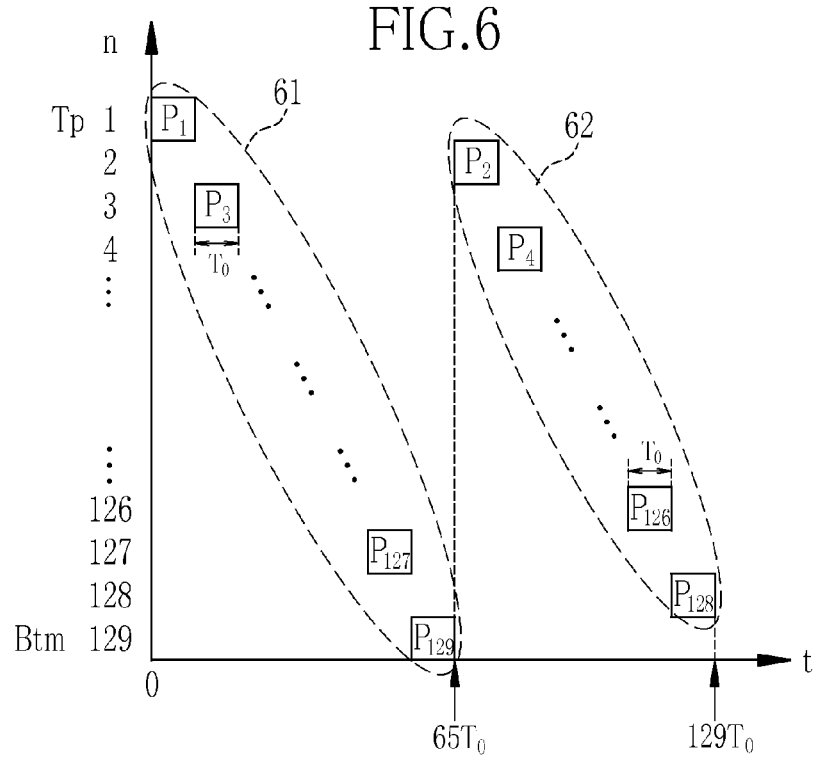
FIG. 5 is a table indicating settings for standard mode and high-speed mode.
FIG. 6 is an explanatory diagram illustrating the sequence for production of tomographic images in the high-speed mode.

As shown in FIG. 6, provided that the reconstruction processor 44 takes a time $T_0$ to produce one tomographic image, it will take a period of time t=$129T_0$ from a start of production of tomographic images (t=0) to complete the production of all tomographic images $P_1$ to $P_{129}$. However, the production of the first group 61 of tomographic images $P_1$, $P_3$, . . . , $P_{127}$, $P_{129}$ for use in the image examination will complete in a period of time t=$65T_0$, as they are produced prior to the second group 62 of tomographic images. Therefore, it is possible to complete the image examination and input the instruction to transmit the tomographic images at any timing after the lapse of time t=$65T_0$. Accordingly, it is possible to complete the image examination at the shortest in half the time (t=$65T_3$) it takes for conventional image examinations which require producing all tomographic images.

The reason why the image examination can be completed in the time t=$65T_0$ is because the first group 61 of tomographic images $P_1$, $P_3$, . . . , $P_{127}$, $P_{129}$ are sorted out according to the number for thinning. That is, by sorting those tomographic images which are to be preferentially produced for the image examination according to the number for thinning, the tomographic images to be preferentially-produced will be selected from the entire range of the subject 14 from the top side Tp thereof (the side facing the radiation source 21) through to the bottom side Btm thereof (the side facing the FPD 22), and at least a preferentially-produced tomographic image will be selected from among those tomographic images which keep a certain similarity to each other. Thus, merely with the first group 61 of tomographic images $P_1$, $P_3$, . . . $P_{127}$, $P_{129}$, it is possible to comprehend the total quality of all tomographic images $P_1$ to $P_{129}$ and complete the image examination precisely and rapidly.

Particularly because the number for thinning is determined by the sweep angle θ, at least a preferentially-produced tomographic image will be selected from those tomographic images which keep a certain similarity to each other. The resolution of tomographic images is improved with an increase in sweep angle θ in the tomosynthesis image acquisition. Therefore, as the sweep angle θ increases, the similarity between tomographic images of adjacent slice positions (n and n+1) decreases. Conversely, as the sweep angle θ decreases, the resolution of tomographic images decreases, so the similarity between tomographic images of adjacent slice positions increases. Since the radiography system 10 sets up the higher number for thinning to the narrower sweep angle θ (the lower number for thinning to the wider sweep angle θ), a tomographic image will be selected for the image examination from every certain ranges within which the tomographic images keep a certain similarity to each other.

When the standard mode is selected, wherein the sweep angle θ is 20 degrees and 129 tomographic images $P_1$ to $P_{129}$ are to be produced (refer to FIG. 5), the number for thinning is "0". That is, the reconstruction processor 44 does not make the thinning but produces all tomographic images $P_1$ to $P_{129}$ in ascending order of n of $P_n$. This is because in the standard mode the sweep angle θ is large (20 degrees) and hence the similarity between the tomographic images $P_n$ is so low that it is impossible to determine the adequacy of an adjacent tomographic image $P_{n+1}$ on the basis of a preceding tomographic image $P_n$ even while the tomographic image $P_n$ is determined to be good.

Figure 7:
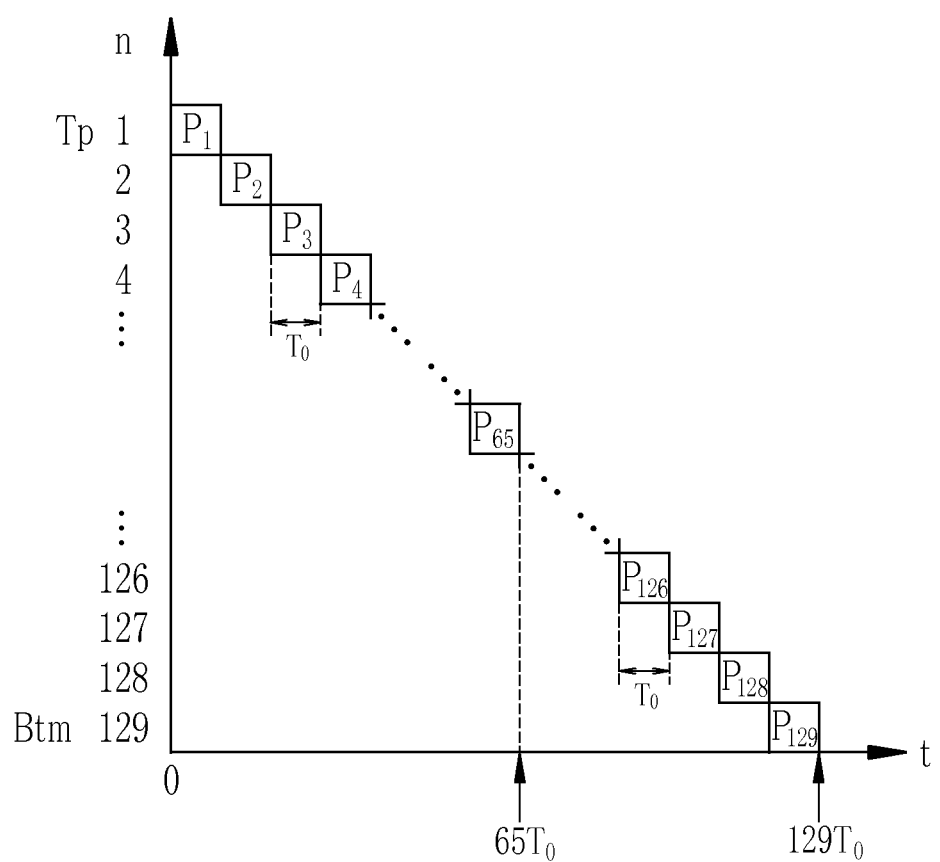
FIG. 7 is an explanatory diagram illustrating the sequence for production of tomographic images in the standard mode.

Accordingly, as shown in FIG. 7, the production of merely tomographic images $P_1$ to $P_{65}$ of half from the top side Tp of the subject 14 will complete at the time $t=65T_0$ in the standard mode, so it is impossible to grasp tomographic images $P_{66}$ to $P_{129}$ of the bottom side Btm of the subject 14 at that time $t=65T_0$. Accordingly, in the standard mode, it requires at least the time $t=129T_0$ to accomplish the image examination. In order to determine the adequacy of the acquired images exactly, it is necessary to check quite a lot of tomographic images of the bottom side Btm. Therefore, even though it may be possible to complete the image examination before a small part (e.g. several) of the tomographic images $P_{66}$ to $P_{129}$ of the bottom side Btm are not yet produced and displayed, it is at least impossible to complete the image examination within the time $t=65T_0$.

Figure 8:
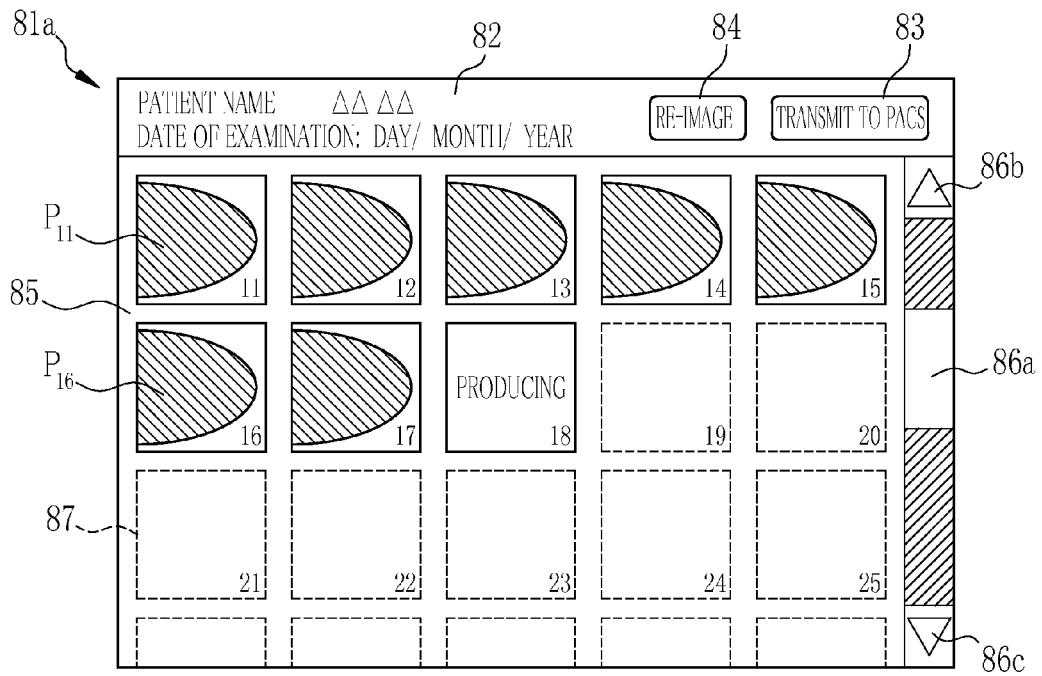
FIG. 8 is a schematic diagram illustrating a display screen for image examination in a case where the number for thinning is "0"

The following description relates to display screens on the display section 42 to be displayed for the image examination. A display screen 81a for the image examination, as shown in FIG. 8, is for a case where all tomographic images $P_n$ are to be produced are displayed for the image examination (i.e. when the number for thinning is "0"). As an example, the screen 81a has an information display zone 82 for displaying name of patient, date of imaging, imaging parameters (not shown), etc., the transmission button 83 for inputting an instruction to transmit the images and the re-imaging button 84 for inputting an instruction for re-imaging. On the screen 81a, the image transmission button 83 and the re-imaging button 84 are enabled after all of the tomographic images $P_n$ are produced and displayed.

The display screen 81a has an image display zone 85 below the information display zone 82, for displaying the tomographic images $P_n$, and has an operation bar 86a and operation buttons 86b and 86c on the right margin of the image display zone 85, for scrolling the image display zone 85 up and down (or switch over the whole content) so as to display those tomographic images $P_n$ which are not presently displayed on the screen.

The image display zone 85 displays a plurality of tomographic images $P_n$ in an array. In a segment where a tomographic image that the reconstruction controller 44 is producing now (e.g. tomographic image $P_{18}$) is going to be displayed next, this information is displayed therein. In those segments where tomographic images $P_n$ to be produced later are expected to be displayed, dummy images 87 are displayed to indicate that there are tomographic images which are not yet produced but will be produced and displayed for the image examination. The dummy image 87 may, for example, be a particular image or an indicia which suggests that the tomographic image to be displayed here is not produced yet, or may be a frame or the like indicating the boundary of each segment in which an individual tomographic image is to be displayed. Numbers displayed at the respective lower-right corners of the displayed tomographic images $P_n$ and the dummy images 87 are the integers "n" that indicate the correlation with the slice positions of the subject 14.

Figure 9:
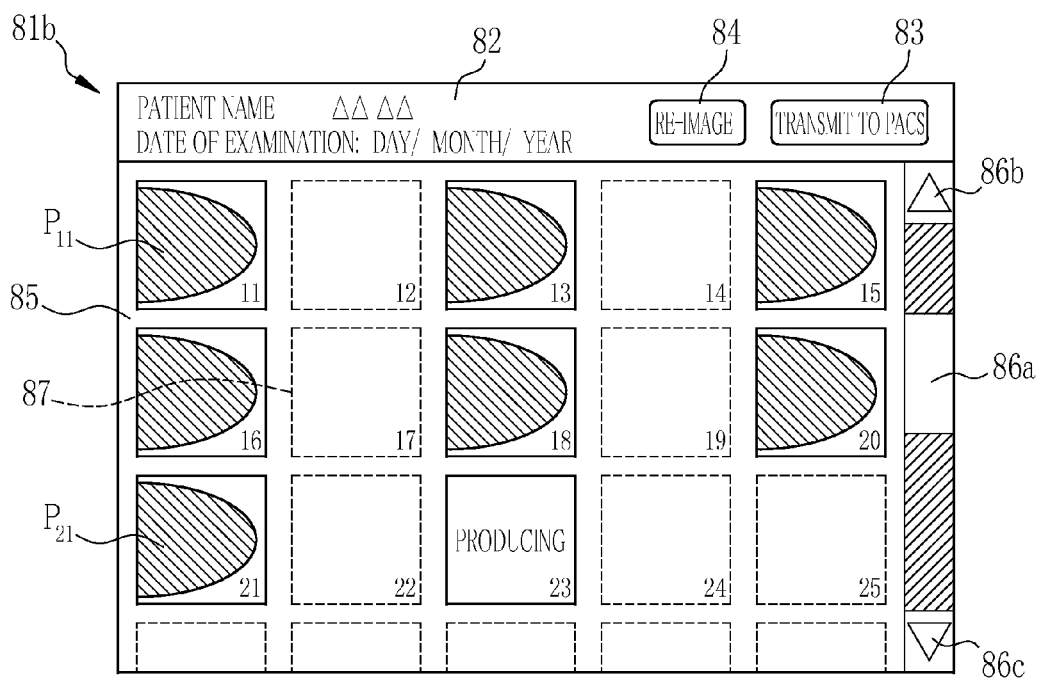
FIG. 9 is a schematic diagram illustrating a display screen for image examination in a case where the number for thinning is "1"

A display screen 81b shown in FIG. 9 is for the image examination in the case where the number for thinning is "1". The display screen 81b is provided with an information display zone 82, a transmission button 83, a re-imaging button 84, an image display zone 85, a tool bar 86a and operation buttons 86b and 86c in the same way as the display screen 81a for the case where the number for thinning is "0". However, because the number for thinning is "1", tomographic images are sequentially displayed only in odd-numbered segments in the image display zone 85. When all of the odd-numbered tomographic images are displayed, the image transmission button 83 and the re-imaging button 84 are enabled.

Figure 10:
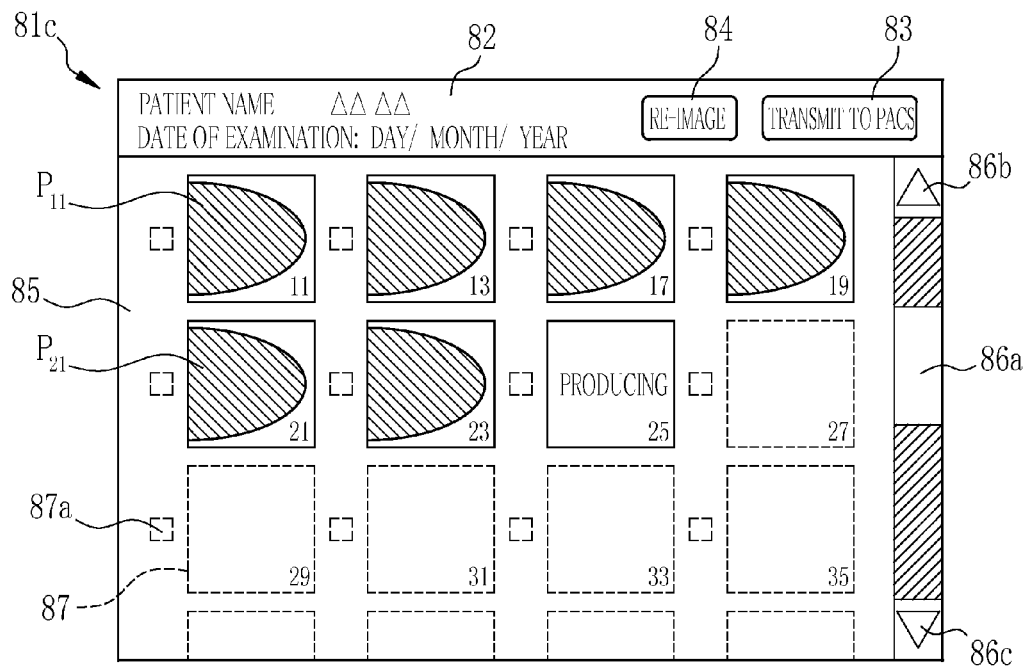
FIG. 10 is a schematic diagram illustrating another display screen for image examination in a case where the number for thinning is "1"

A display screen 81c shown in FIG. 10 is a modified screen for the image examination in the case where the number for thinning is "1", wherein small dummy images 87a are displayed in place of even-numbered (the second group of) tomographic images which are not produced and displayed at the time of image examination. This screen enables displaying a higher number of odd-numbered (the first group of) tomographic images in a row, facilitating the image examination.

Figure 11:
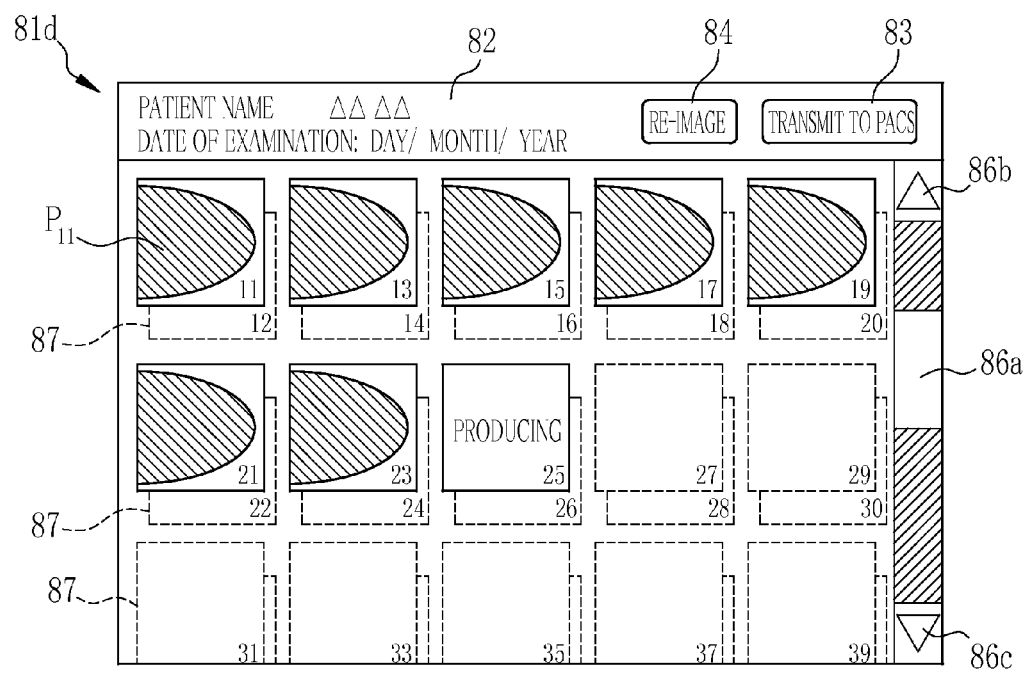
FIG. 11 is a schematic diagram illustrating still another display screen for image examination in a case where the number for thinning is "1"

A display screen 81d shown in FIG. 11 is another modified screen for the image examination in the case where the number for thinning is "1", wherein the dummy images 87 for the even-numbered tomographic images, which are not produced and displayed at the time of image examination, are displayed behind the odd-numbered tomographic images (or behind the dummy images 87 for the odd-numbered tomographic images) in a manner partly overlap each other. This screen also enables displaying a higher number of odd-numbered tomographic images in a row, facilitating the image examination.

Figure 12:
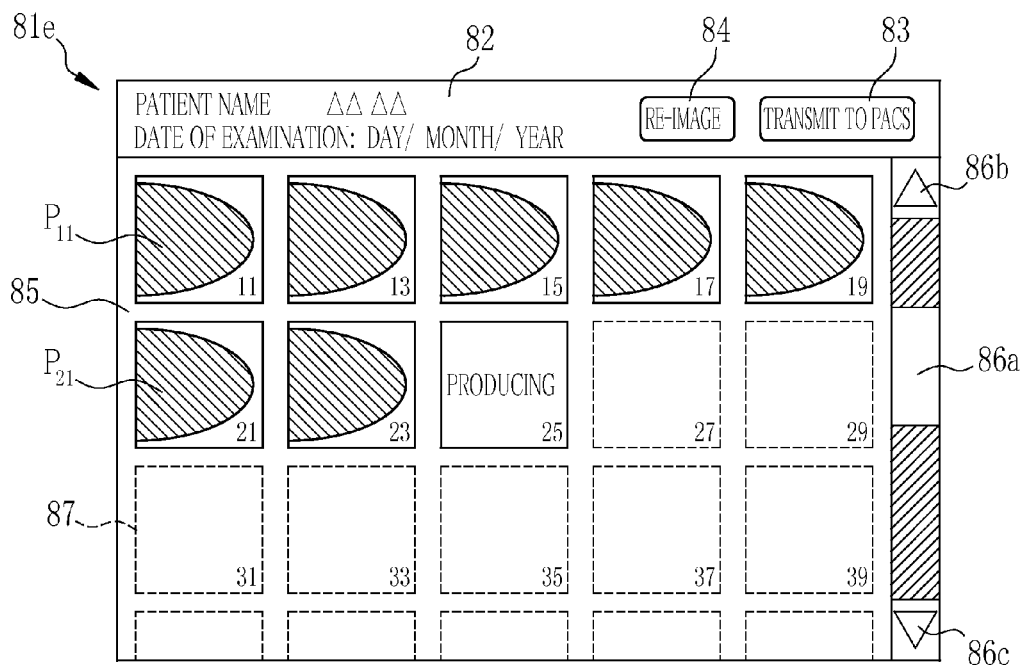
FIG. 12 is a schematic diagram illustrating an alternative display screen for image examination in a case where the number for thinning is "1"

A display screen 81e shown in FIG. 12 is still another modified screen for the image examination in the case where the number for thinning is "1", wherein the odd-numbered tomographic images used for the image examination and the dummy images 87 therefor are displayed exclusively. By omitting displaying the even-numbered tomographic images which are not used for the image examination and the dummy images therefor, the display screen 81e provides approximately the same screen layout as the display screen 81a for the image examination in the case where the number for thinning is "0", as shown in FIG. 8. Thus, the usability is stabilized regardless of the number for thinning.

Figure 13:
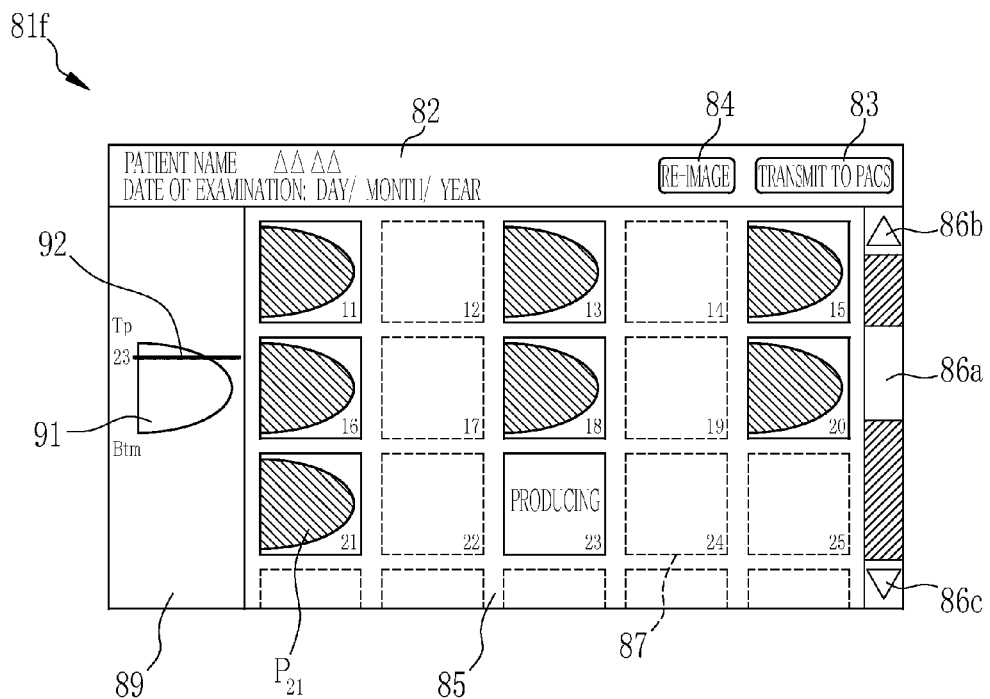
FIG. 13 is a schematic diagram illustrating a further alternative display screen for image examination in a case where the number for thinning is "1".

FIG. 13 shows a display screen 81f as another modification of screen for the image examination in the case where the number for thinning is "1", wherein a correlation display zone 89 for showing the correlation between the subject 14 and the tomographic images is provided on the left side of the image display zone 85. For example, the correlation display zone 89 displays a schematic diagram 91 of the subject 14 and a line 92 that indicates the slice position through the subject 14 of a tomographic image that is being produced (e.g. tomographic image $P_{23}$). This enables grasping the progress of production of tomographic images $P_n$ without the need for scrolling the image display zone 85. A projection image or a photographic picture of the subject 14 or the like may be used in place of the schematic diagram 91.

It is also possible to make the line 92 movable relative to the schematic diagram 91 such that the image display zone 85 automatically scrolls to display a tomographic image (or the dummy image 87 therefor) which corresponds to a slice position indicated by the moved line 92 in the image display zone 85 if the corresponding tomographic image (or the dummy image 87 therefor) is not displayed before the line 92 is moved. In FIG. 13, the image display zone 85 of the display screen 81f has the same display pattern as the image display zone 85 of the display screen 81b shown in FIG. 9, but the display pattern in the image display zone 85 of the display screen 81f may also be any of those of the display screens 81c to 81e shown in FIGS. 10 to 12.

In the examples where the dummy images 87 or 87a are displayed in the image display zone 85, as with the display screens 81a to 81d and 81f in FIGS. 8 to 11 and 13, it may be possible to configure the dummy images 87 or 87a to be selectable such that, if a dummy image 87 or 87a is selected, the production of a tomographic image that is expected to be produced next in the predetermined order is interrupted, and a tomographic image corresponding to the selected dummy image 87 or 87a is produced and displayed before. Thus, the radiologist is enabled to select a tomographic image of an arbitrary slice position to be produced and displayed if the radiologist determines it necessary to examine the selected tomographic image preferentially or specifically, and therefore the accuracy of the image examination is improved.

In the above examples, if the number for thinning is "1", the reconstruction controller 44 produces odd-numbered tomographic images $P_1, P_3, P_5, \ldots$ sequentially from the first tomographic image $P_1$ (n=1) as the first group 61 of tomographic images to be produced preferentially for the image examination. However, it is possible to produce even-numbered tomographic images $P_2, P_4, P_6, \ldots$ as the first group 61 of tomographic images preferentially for the image examination without producing the first tomographic image $P_1$. In other words, every second tomographic image may only be produced preferentially for the image examination if the number for thinning is "1". If the number for thinning is "2", the first group of tomographic images to be produced preferentially for the image examination may be one of three groups of tomographic images, including tomographic images $P_1, P_4, P_7, \ldots$, tomographic images $P_2, P_5, P_8, \ldots$ and tomographic images $P_3, P_6, P_9, \ldots$. The same applies to each case where the number for thinning is not less than three.

Although the reconstruction controller 44 produces the tomographic images $P_n$ in ascending order of n (in the order from the side facing the radiation source 21), it is alternatively possible to produce the tomographic images $P_n$ in the reversed order, sequentially from the side facing the FPD 22. It may also be possible to switch over the order therebetween depending on the setups.

For a tomosynthesis image acquisition, the radiation source 21 is moved intermittently at constant intervals from the position $S_1$ to the position $S_M$ in the above example. However, the intervals of movement of the radiation source 21 are not limited to be constant. For example, the radiation source 21 may be moved at intervals corresponding to an angle $2\theta/M$. The same applies to the intervals of movement of the FPD 22.

In addition, the imaging controller 31 automatically determines the number M of projection images to be obtained for a tomosynthesis image acquisition and the intervals of intermittent movement of the radiation source 21 according to the sweep angle $\theta$ of the radiation source 21 and the number N of tomographic images to be produced, etc., which are designated as imaging parameters, but the number M of projection images and the intervals of intermittent movement may be designated as imaging parameters, so as to determine the sweep angle $\theta$ and the number N according to these values.

Although the process sequence controller 45 calculates the number for thinning from the sweep angle obtained as an imaging parameter with reference to the LUT 46, the number for thinning may also be set up by the radiologist. In that case, the number for thinning is, for example, calculated according a predetermined function that uses the sweep angle as variable. The predetermined function for calculating the number for thinning is configured to output the greater value as the number for thinning, the smaller the value input as the sweep angle is.

Furthermore, it is possible for the radiologist to set up the number for thinning selectively within a range corresponding to the sweep angle. In that case, the upper limit of the selectable numbers for thinning is preferably set to be raised with decreasing sweep angle. This is for preventing the number for thinning from being set so high that the accuracy of the image examination is reduced.

Although the process sequence controller 45 obtains information on the sweep angle of the radiation source 21 as imaging parameters from the input section 41, it is possible to obtain the sweep angle from the meta-information written on the header of a set of projection images. It is also possible to obtain the sweep angle of the radiation source 21 from the imaging unit 11 (imaging controller 31), etc. Furthermore, the process sequence controller 45 may obtain the sweep angle at any time before the production of tomographic images. For example, information on the sweep angle may be obtained after a set of projection images being obtained.

The radiography system 10 predetermines the standard mode and the high-speed mode as the preset imaging modes (refer to FIG. 5), but may be provided with other imaging modes with different sweep angles and numbers for thinning. It is also possible to predetermine the standard mode or the high-speed mode as only one preset imaging mode.

When an instruction to transmit the produced tomographic images $P_n$, the console 13 produces the second group of tomographic images in the background, and the tomographic images $P_n$ are transmitted to the PACS 52 after the production of all tomographic images $P_n$ to be produced. It is, however, unnecessary to wait for the completion of production of the second group of tomographic images, before transmitting the tomographic images to the PACS 52. For example, the first group of tomographic images, which have already been produced when an instruction to transmit the images is input, may be transmitted to the PACS 52 before the second group of tomographic images, and tomographic images of the second group may be sequentially transmitted to the PACS 52 as soon as each image is produced in the background.

The subject 14 is a breast mass in the above examples, but the subject 14 is an arbitrary subject; the subject 14 may be a site of a living body other than a breast mass, or may also be non-biological subject. Furthermore, in the present embodiment, the imaging unit 11 is digital mammography equipment since the subject 14 is a breast mass, but the imaging unit 11 may be replaced with any device, for example according to the subject 14, insofar as the device is capable of tomosynthesis image acquisitions. However, the imaging unit 11 must be a device that is capable of tomosynthesis image acquisitions. For example, a so-called X-ray computed tomography scanner irradiates a subject with X-rays sequentially from all directions around the subject in order to scan the subject to produce tomographic images thereof. That is, in an X-ray computed tomography scanner, the sweep angle of an X-ray radiation source is typically fixed at 360 degrees and hence the feature of changing the sweep angle θ like in the radiography system 10 is not available. Therefore, it is impossible to replace the imaging unit 11 with an X-ray computed tomography scanner.

Although the radiation source 21 and the FPD 22 are moved in parallel to each other for the tomosynthesis image acquisition, it is alternatively possible to rotate the radiation source 21 and the FPD 22 semi-circularly around a subject so as to acquire images of the subject at multiple angles.

Although the FPD 22 is mounted to be movable and moved in synchronism with the radiation source 21 for the tomosynthesis image acquisition, a stationary FPD is usable if the stationary FPD is large enough to cover the entire range 0 of the sweep angle θ of the radiation source 21.

The display section 42 displays such tomographic images $P_n$ that are used as they are for the diagnosis, but the display section 42 may also display thumbnails of the tomographic images $P_n$ unless the thumbnails of the tomographic images $P_n$ lower the accuracy of the image examination down below a necessary level.

The FPD 22 is an indirect-conversion type which converts incident X-rays into visible light and thereafter photoelectrically converts the visible light into electrical signal, but an FPD of a direction-conversion type which coverts incident X-rays directly into electrical signal is suitably usable in the radiography system 10. There are surface-incident FPDs and rear-surface-incident FPDs, which are known to have different internal layered-structures. Insofar as it is capable of obtaining projection images, the FPD 22 may have any internal structure.

Although the radiation source 21 is an X-ray radiation source, other kinds of radioactive rays than X-rays may be applicable.

A radiography control program for operating a radiography system, which is provided with the radiation source 21, the FPD 22, the reconstruction controller 44, the process sequence controller 45 and the display section 42, in the manner as described in the above embodiments is another aspect of the present invention.

While the present invention has been described with reference to preferred embodiments, those skilled in the art will appreciate that various alternations and modifications may be made to the embodiments without departing from the spirit of the invention. Accordingly, the foregoing description is meant to be exemplary only, and should not limit the scope of the invention as set forth in the claims.

What is claimed is:

1. A radiography system comprising:
    a radiation source mounted movable to multiple positions of different projection angles relative to an imaging subject which is placed at a predetermined position;
    a radiographic image detector which detects a radiographic image of the subject by detecting radioactive rays that have penetrated the subject;
    an imaging controller which controls the radiation source to move within a range of a designated sweep angle and project radioactive rays toward the subject at different projection angles, while controlling the radiographic image detector to detect a set of radiographic images each at a different projection angle;
    a reconstruction processor which reconstructs the set of radiographic images of the subject acquired at multiple projection angles so as to produce a plurality of tomographic images of the subject, which are used for diagnosis;
    a process sequence controller which determines a parameter for sorting the plurality of tomographic images into a first group and a second group according to the sweep angle and controls the reconstruction processor on the basis of the parameter so as to produce the first group of tomographic images prior to the second group of tomographic images; and
    a display device which displays at least the first group of tomographic images for determination on whether the tomographic images are adequate for use in diagnosis.

2. The radiography system set forth in claim 1, wherein the process sequence controller determines the parameter such that the first group of tomographic images are selected from the plurality of tomographic images at intervals of a predetermined number.

3. The radiography system set forth in claim 1, wherein the process sequence controller determines the parameter such that the number of tomographic images included in the first group decreases with the smaller sweep angle.

4. The radiography system set forth in claim 2, which is provided with at least two imaging modes, including a first imaging mode wherein the sweep angle is set at a predetermined value, and a second imaging mode wherein the sweep angle is set at a smaller value than in the first imaging mode, wherein,
    the process sequence controller preferably determines the parameter such that the number of tomographic images included in the first group is reduced in the second imaging mode in comparison with the first imaging mode.

5. The radiography system set forth claim 4, wherein the process sequence controller determines the parameter such that all of the plurality of tomographic images are sorted into the first group when the first imaging mode is selected.

6. The radiography system set forth claim 1, wherein when it is determined on the basis of the first group of tomographic images displayed on the display device that the tomographic images are adequate for use in diagnosis, the display device displays a screen for making another image acquisition and the reconstruction processor produces the second group of tomographic images in the background.

7. The radiography system set forth claim 1, wherein when it is determined on the basis of the first group of tomographic images displayed on the display device that the tomographic images are inadequate for use in diagnosis, the reconstruction processor quits producing the second group of tomographic images.

8. A radiography method comprising:
- an imaging step wherein a radiation source, which is mounted movable to multiple positions of different projection angles relative to an imaging subject placed at a predetermined position, is moved within a range of a designated sweep angle while projecting radioactive rays toward the subject at different projection angles, and a radiographic image detector detects a set of radiographic images each at a different projection angle;
- a parameter calculation step wherein a parameter is determined according to the sweep angle, the parameter being for sorting a plurality of tomographic images to be produced in a tomographic image production step into a first group and a second group;
- the tomographic image production step wherein a plurality of tomographic images of the subject, which are used for diagnosis, are produced by reconstructing the set of radiographic images acquired from the subject at multiple projection angles, and wherein the plurality of tomographic images to be produced are sorted into the first group and the second group according to the parameter, and the first group of tomographic images are produced prior to the second group of tomographic images; and
- a tomographic image display step wherein at least the first group of tomographic images are displayed for determination on whether the tomographic images are adequate for use in diagnosis or not.

* * * * *